(12) United States Patent
Furuhata

(10) Patent No.: US 10,666,854 B2
(45) Date of Patent: May 26, 2020

(54) BENDING OPERATION CONTROL FOR ENDOSCOPE

(71) Applicant: OLYMPUS CORPORATION, Tokyo (JP)

(72) Inventor: Tsuyoshi Furuhata, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 25 days.

(21) Appl. No.: 16/027,649

(22) Filed: Jul. 5, 2018

(65) Prior Publication Data
US 2018/0324352 A1    Nov. 8, 2018

Related U.S. Application Data

(63) Continuation of application No. PCT/JP2016/088823, filed on Dec. 27, 2016.

(30) Foreign Application Priority Data

Jan. 8, 2016  (JP) .................................. 2016-002788

(51) Int. Cl.
*H04N 5/232*     (2006.01)
*A61B 1/00*      (2006.01)
(Continued)

(52) U.S. Cl.
CPC ..... *H04N 5/23216* (2013.01); *A61B 1/00006* (2013.01); *A61B 1/00009* (2013.01); *A61B 1/00039* (2013.01); *A61B 1/00045* (2013.01); *A61B 1/0051* (2013.01); *A61B 1/00096* (2013.01); *G02B 23/2476* (2013.01); *G06F 3/0338* (2013.01); *G06F 3/0487* (2013.01);
(Continued)

(58) Field of Classification Search
CPC ........................... A61B 1/00039; H04N 5/232
See application file for complete search history.

(56) References Cited

U.S. PATENT DOCUMENTS

2004/0267093 A1* 12/2004 Miyagi .............. A61B 1/00039
                                                          600/146
2008/0262311 A1* 10/2008 Itou .................... A61B 1/00039
                                                          600/152
(Continued)

FOREIGN PATENT DOCUMENTS

JP      2013-137466 A     7/2013
JP      2014-6481 A       1/2014
(Continued)

OTHER PUBLICATIONS

International Search Report dated Apr. 11, 2017 received in PCT/JP2016/088823.

*Primary Examiner* — Rowina J Cattungal
(74) *Attorney, Agent, or Firm* — Scully, Scott, Murphy & Presser, P.C.

(57) ABSTRACT

An endoscope apparatus determines whether a first instruction input by an operation section is detected, performs first operation control on a bending section when determining that the first instruction input is detected, determines whether a second instruction input by a touch panel is detected, and performs second operation control different from the first operation control on the bending section when determining that the second instruction input is detected.

10 Claims, 10 Drawing Sheets

(51) Int. Cl.
*G06F 3/0487* (2013.01)
*A61B 1/005* (2006.01)
*G02B 23/24* (2006.01)
*G06F 3/0338* (2013.01)
*G06F 3/0488* (2013.01)
*A61B 1/04* (2006.01)
*H04N 5/225* (2006.01)

(52) U.S. Cl.
CPC ..... *G06F 3/04883* (2013.01); *H04N 5/23293* (2013.01); *A61B 1/04* (2013.01); *G02B 23/2484* (2013.01); *H04N 2005/2255* (2013.01)

(56) References Cited

U.S. PATENT DOCUMENTS

| | | | |
|---|---|---|---|
| 2008/0275303 A1* | 11/2008 | Koitabashi | A61B 1/0052 600/146 |
| 2009/0149709 A1* | 6/2009 | Koitabashi | A61B 1/00039 600/131 |
| 2011/0208000 A1* | 8/2011 | Honda | A61B 1/00016 600/118 |
| 2014/0005931 A1 | 1/2014 | Ono et al. | |

FOREIGN PATENT DOCUMENTS

| | | | |
|---|---|---|---|
| JP | 2014-109630 A | | 6/2014 |
| JP | 2014109630 A | * | 6/2014 |
| WO | 2013/099305 A1 | | 7/2013 |
| WO | WO-2013099305 A1 | * | 7/2013 |

* cited by examiner

BENDING OPERATION CONTROL FOR ENDOSCOPE

CROSS REFERENCE TO RELATED APPLICATION

This application is a continuation application of PCT/JP2016/088823 filed on Dec. 27, 2016 and claims benefit of Japanese Application No. 2016-002788 filed in Japan on Jan. 8, 2016, the entire contents of each of which are incorporated herein by their reference.

BACKGROUND

1. Technical Field

The present invention relates to an endoscope apparatus, an operation control method for the endoscope apparatus, and a storage medium having an operation control program for the endoscope apparatus stored therein.

2. Background Art

Conventionally, endoscope apparatuses have been widely used in an industrial field and a medical field. For example, as disclosed in Japanese Patent Application Laid-Open Publication No. 2014-109630, an endoscope apparatus is proposed that inserts an insertion section including a bending section into an object, gives a bending motion instruction to the bending section through a touch panel to cause the bending section to perform a bending motion, picks up an image of the object from a distal end of the insertion section, and displays an endoscopic image in an image display region.

SUMMARY

An endoscope apparatus according to an aspect of the present invention includes: a display device configured to display an endoscopic image obtained by picking up an image of an object with an image pickup section; a touch panel provided in the display device; an insertion section including a bendable bending section; an operation section including at least one operation device; and a processor. The processor determines whether a first instruction input by the operation section is detected, performs first operation control on the bending section when determining that the first instruction input is detected, determines whether a second instruction input by the touch panel is detected, and performs second operation control different from the first operation control on the bending section when determining that the second instruction input is detected.

An operation control method for an endoscope apparatus according to an aspect of the present invention includes: determining whether a first instruction input by an operation section including at least one operation device is detected; performing first operation control on a bendable bending section provided in an insertion section when determining that the first instruction input is detected; determining whether a second instruction input by a touch panel provided in a display device configured to display an endoscopic image obtained by picking up an image of an object with an image pickup section is detected; and performing second operation control different from the first operation control on the bending section when determining that the second instruction input is detected.

A storage medium according to an aspect of the present invention stores an operation control program for an endoscope apparatus, the operation control program causing a computer to execute: a code for determining whether a first instruction input by an operation section is detected; a code for performing first operation control on a bending section when determining that the first instruction input is detected; a code for determining whether a second instruction input by a touch panel is detected; and a code for performing second operation control different from the first operation control on the bending section when determining that the second instruction input is detected.

DETAILED DESCRIPTION OF THE PREFERRED EMBODIMENTS

Embodiments of the present invention are explained below with reference to the drawings.

First Embodiment (Configuration)

Figure 1:
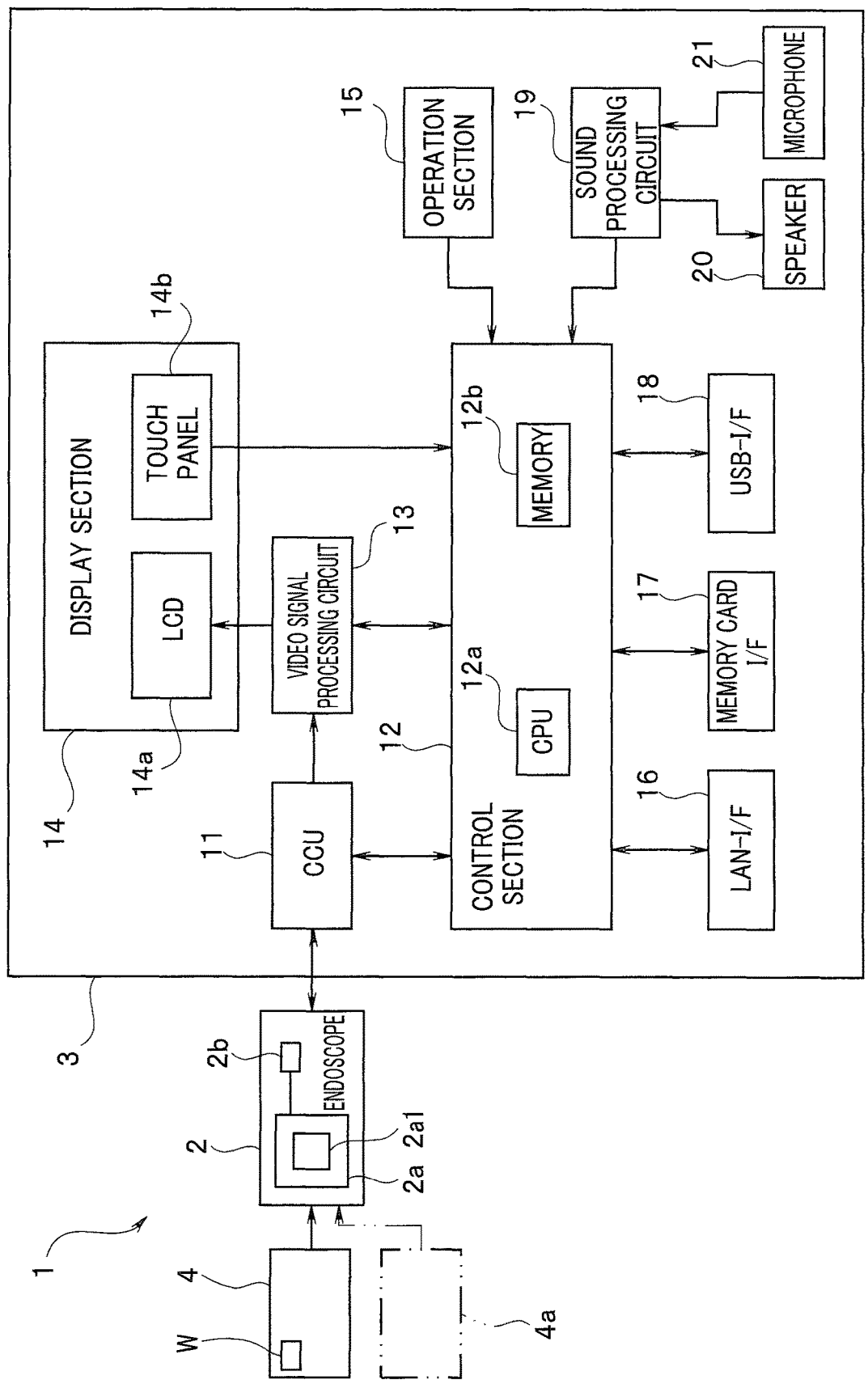
FIG. 1 is a block diagram showing a configuration of an endoscope apparatus according to a first embodiment of the present invention.

FIG. 1 is a block diagram showing a configuration of an endoscope apparatus 1 according to a first embodiment of the present invention.

The endoscope apparatus 1 includes an endoscope 2, which is an image pickup section, and an apparatus body 3 to which the endoscope 2 is connected.

The endoscope 2 is configured to be inserted into a test target and capable of picking up an image of an object in the test target. The endoscope 2 is connected to the apparatus body 3. The endoscope 2 is configured to be controlled by the apparatus body 3 and capable of outputting an image pickup signal to the apparatus body 3. The endoscope 2 includes an insertion section 2a and an actuator 2b.

The insertion section 2a is formed in an elongated shape to be insertable into the test target. An optical adapter 4 including an observation window W is attached to a distal end portion of the insertion section 2a. The insertion section 2a includes a bendable bending section 2a1 on a proximal end side of the distal end portion. The bending section 2a1 is connected to the actuator 2b.

The actuator 2b is connected to a control section 12 via a camera control unit (hereinafter referred to as "CCU") 11 of the apparatus body 3 and is capable of causing, on the basis of control by the control section 12, the bending section 2a1 to perform a bending motion. The actuator 2b is capable of switching the bending section 2a1 to either one of an angle lock state and an angle unlock state on the basis of the control by the control section 12. The actuator 2b has state information including the angle lock/angle unlock state and a power supply ON/OFF state. The state information is configured to be referable from the control section 12.

The angle lock state is a state in which a bending angle of the bent bending section 2a1 is fixed to prevent a bending angle of the bending section 2a1 from changing with an external force. The angle unlock state is a state in which the angle lock state of the bending section 2a1 is released and is a state in which the bending section 2a1 can be freely bent. For example, when an object includes a bent insertion path, the insertion section 2a is inserted into the object in the angle unlock state. The bending section 2a1 is bent in the angle lock state to be directed to the object and picks up an image of the object. After the image pickup of the object, the bending section 2a1 is pulled out from the object in the angle unlock state.

The apparatus body 3 includes the CCU 11, the control section 12, a video signal processing circuit 13, a display section 14, an operation section 15, a LAN interface (hereinafter referred to as "LAN-I/F") 16, a memory card interface (hereinafter referred to as "memory card I/F") 17, a USB interface (hereinafter referred to as "USB-I/F") 18, a sound processing circuit 19, a speaker 20, and a microphone 21.

The CCU 11 is a circuit configured to control the endoscope 2, which is the image pickup section. Under the control by the control section 12, the CCU 11 drives a not-shown image pickup device of the endoscope 2 and receives an image pickup signal outputted from the image pickup device and outputs the image pickup signal to the video signal processing circuit 13.

The control section 12 includes a central processing unit (hereinafter referred to as "CPU") 12a and a memory 12b including a RAM and a ROM. The control section 12 is configured to be capable of receiving signals from various circuits in the endoscope apparatus 1 and outputting control signals to the various circuits. For example, the control section 12 is capable of receiving a control signal from the actuator 2b and detecting possibility of driving of the actuator 2b and possibility of the bending motion of the bending section 2a1.

The memory 12b is capable of storing various programs concerning operation control and various setting data used in the operation control. The various setting data includes movement amounts da and db of an endoscopic image explained below.

The movement amount da of the endoscopic image is an amount corresponding to a unit moving distance of a finger on a touch panel 14b of the display section 14 in a first operation method, that is, an operation method of stroking the touch panel 14b. That is, the movement amount da of the endoscopic image is specified as a function of a moving distance of the finger on the touch panel 14b.

The movement amount db of the endoscopic image is an amount corresponding to a contact time period of the finger on the touch panel 14b in a second operation method, that is, an operation method of tapping the touch panel 14b. That is, the movement amount db of the endoscopic image is specified as a function of the contact time period of the finger on the touch panel 14b.

When a first instruction input by the first operation method is performed on the touch panel 14b, the control section 12 performs first operation control, which is control of operation based on the first instruction input. When a second instruction input by the second operation method is performed on the touch panel 14b, the control section 12 performs second operation control, which is control of operation based on the second instruction input.

That is, when the first instruction input by the first operation method is performed on the touch panel 14b, which is a first instruction input section, the control section 12 performs the first operation control, which is the control of operation based on the first instruction input. When the second instruction input by the second operation method is performed on the touch panel 14b, which is a second instruction input section disposed in the display section 14, the control section 12 performs the second operation control, which is the control of operation based on the second instruction input.

More specifically, when an instruction input by the operation method of stroking the touch panel 14b is performed, by causing the bending section 2a1 to perform the bending motion in a stroking direction of the touch panel 14b, the control section 12 moves an image pickup range of the object and brings the bending section 2a1 into the angle unlock state.

Still more specifically, when the instruction input by the operation method of stroking the touch panel 14b is performed, the control section 12 causes, on the basis of the movement amount da, the bending section 2a1 to perform the bending motion such that a display range of the object on an endoscopic image displayed on a liquid crystal display (hereinafter referred to as "LCD") 14a moves from a contact end position toward a contact start position of the finger and according to a distance from the contact end position to the contact start position of the finger. The control section 12 brings the bending section 2a1 into the angle unlock state.

Figure 3:
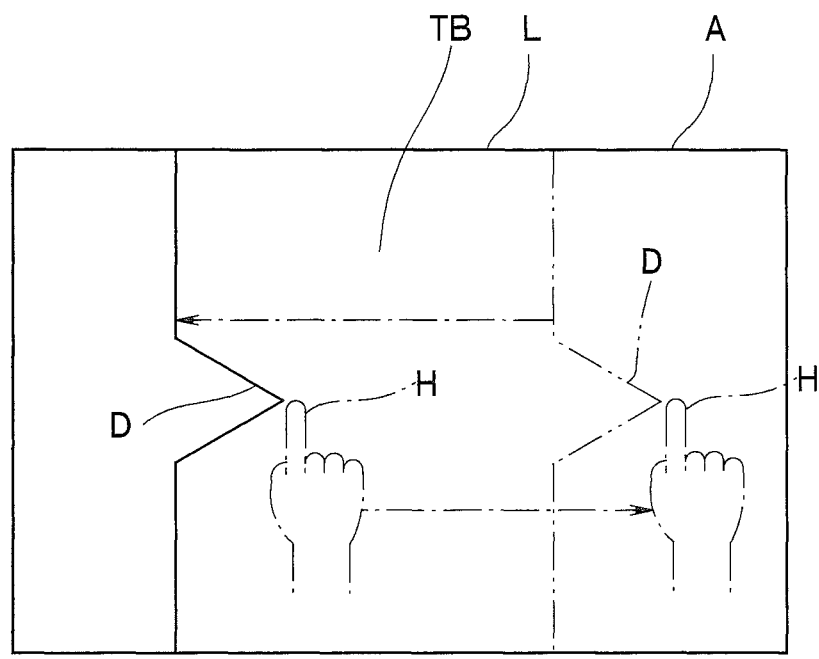
FIG. 3 is a diagram showing an example of the live image displayed on a display section of the endoscope apparatus according to the first embodiment of the present invention.
Figure 4:
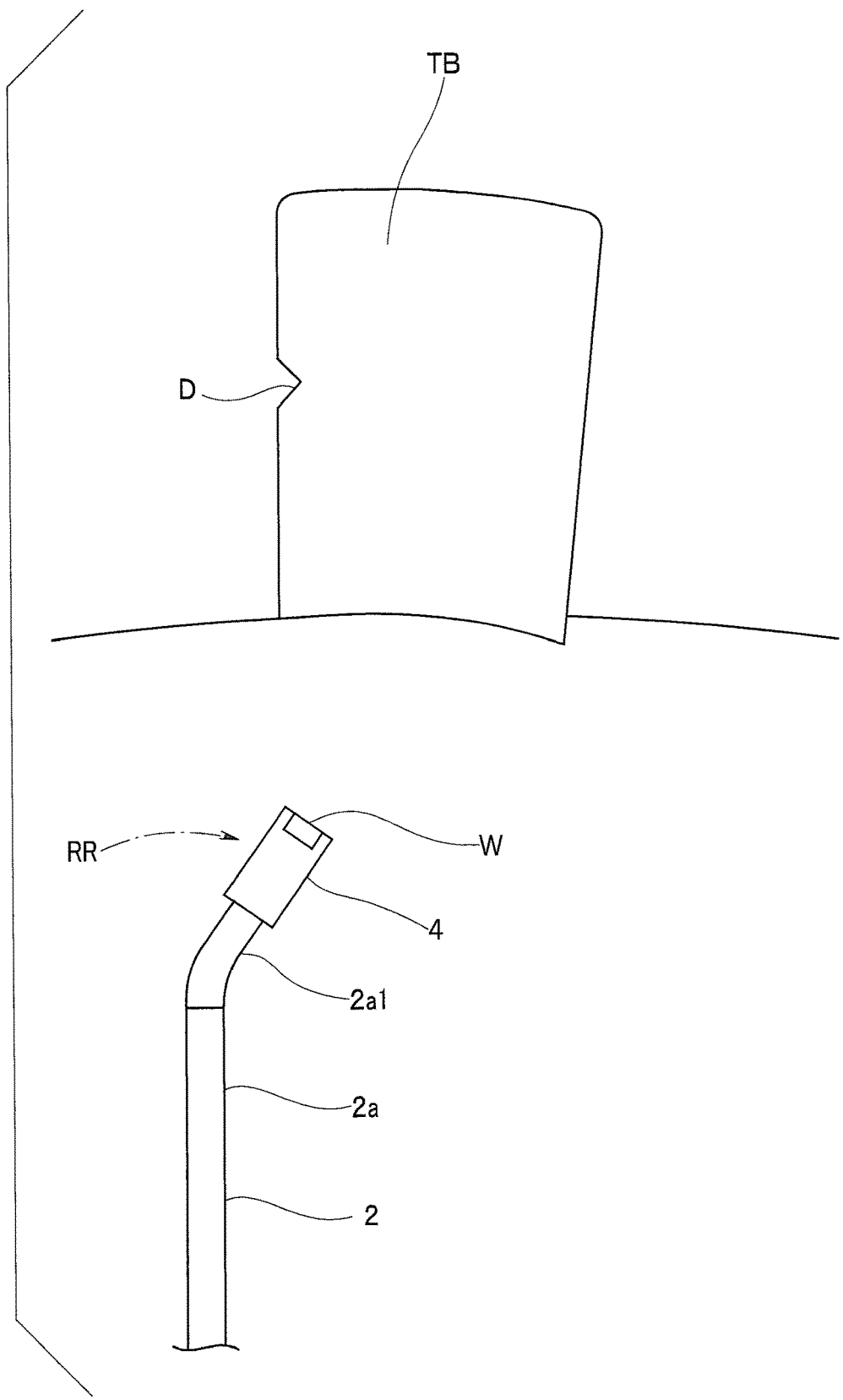
FIG. 4 is a diagram schematically showing an example of a bending motion of a bending section of the endoscope apparatus according to the first embodiment of the present invention.

For example, when the touch panel 14b is stroked from a left portion to a right portion (FIG. 3), the bending section 2a1 performs the bending motion to turn to the right (RR in FIG. 4). Consequently, a turbine blade TB including a chip D moves from a right portion to a left portion on the LCD 14a (FIG. 3). Note that, when the stroking operation is performed, if the bending section 2a1 moves beyond a bendable region, the control section 12 may perform angle unlock after the bending section 2a1 performs the bending motion to a limit position of the bendable region.

On the other hand, when an instruction input by the operation method of tapping the touch panel 14b is performed, by causing the bending section 2a1 to perform the bending motion such that the bending section 2a1 turns to a tapped position of the touch panel 14b, the control section 12 moves the image pickup range of the object and brings the bending section 2a1 into the angle lock state.

Still more specifically, when the instruction input by the operation method of tapping the touch panel 14b is performed, the control section 12 causes, on the basis of the movement amount db, the bending section 2a1 to perform the bending motion such that the tapped position is placed in a center of an image display region A of the display section 14 and the display range of the object on the endoscopic image moves according to a contact time period of the touch panel 14b. The control section 12 brings the bending section 2a1 into the angle lock state.

Figure 5:
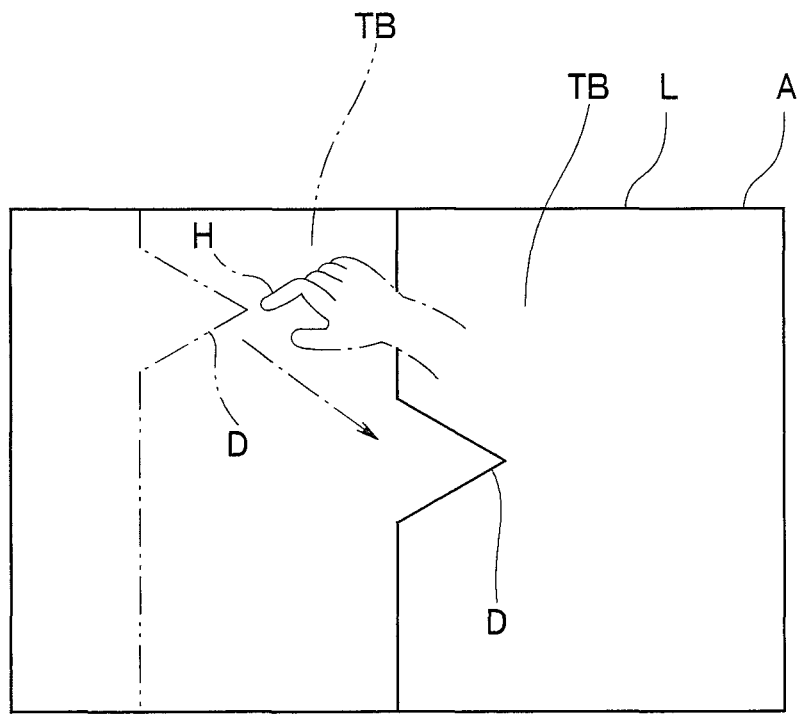
FIG. 5 is a diagram showing an example of the live image displayed on the display section of the endoscope apparatus according to the first embodiment of the present invention.

For example, when the chip D of the turbine blade TB in an upper left portion of the touch panel 14b is tapped, the bending section 2a1 performs the bending motion to turn to upper left. Consequently, the chip D moves from the upper left portion to a center portion (FIG. 5). Note that, when the tapped position is beyond the bendable region, the control section 12 may bring the bending section 2a1 into the angle lock state after the bending section 2a1 performs the bending motion to a limit position where the bending section 2a1 can perform the bending motion toward the tapped position.

The operation method of stroking the touch panel 14b is an operation method in which the distance from the contact end position to the contact start position of the finger on the touch panel 14b is equal to or larger than a predetermined distance. The operation method of stroking the touch panel 14b includes, for example, swipe (an operation method of slipping the finger on the touch panel 14b), flick (an operation method of flicking the finger to slide the finger only a short distance on the touch panel 14b), and drag (an operation method of sliding the finger on the touch panel 14b while keeping touching, for example, a not-shown icon or the like with the finger).

The operation method of tapping the touch panel 14b is an operation method in which the distance from the contact end position to the contact start position of the finger on the touch panel 14b is smaller than the predetermined distance. The operation method of tapping the touch panel 14b includes, for example, tap (an operation method of tapping the touch panel 14b with the finger) and long tap (an operation method of pressing the touch panel 14b with the finger for a long time period).

Note that, when an instruction input by the touch panel 14b is detected, an instruction input with the contact time period of the finger shorter than a predetermined time period may be excluded such that wrong operations can be prevented, for example, when the finger touches the touch panel 14b by mistake only for a very short time period.

The video signal processing circuit 13 is capable of processing an image pickup signal inputted from the CCU 11, generating an endoscopic image, and outputting the endoscopic image to the display section 14. The video signal processing circuit 13 executes image processing corresponding to various functions under the control by the control section 12.

The image display region A is disposed on the display section 14. The display section 14 is configured to be capable of displaying, in the image display region A, an endoscopic image obtained by picking up an image of the object with the endoscope 2. The display section 14 includes the LCD 14a and the touch panel 14b.

The LCD 14a is capable of displaying, in the image display region A, an endoscopic image inputted from the CCU 11.

With the touch panel 14b, an instruction input by the stroking operation method and an instruction input by the tapping operation method can be performed. The touch panel 14b is configured by, for example, the touch panel 14b of an electrostatic type and is provided in close contact with a screen of the LCD 14a. The touch panel 14b is connected to the control section 12. When the finger touches the touch panel 14b, the touch panel 14b outputs a position signal to the control section 12.

The operation section 15 includes a joystick J and a plurality of operation devices such as a freeze button, a release button, a smooth operation method button, and a menu button not shown in the figures.

The LAN-I/F 16 is an interface for connection to a local area network (hereinafter referred to as "LAN"). The endoscope apparatus 1 can perform, via the LAN-I/F 16, communication with an external device connected to the LAN.

The memory card I/F 17 is an interface for attaching a memory card functioning as a storage medium. The endoscope apparatus 1 can read various data such as an endoscopic image from and write the various data in the memory card via the memory card I/F 17.

The USB-I/F 18 is an interface for connecting a USB (universal serial bus) cable or a USB device. The endoscope apparatus 1 can read various data such as an endoscopic image from and write the various data in the USB device via the USB-I/F 18.

Under the control by the control section 12, the sound processing circuit 19 processes a sound signal inputted from the control section 12 and outputs the sound signal to the speaker 20 and processes a sound signal inputted from the microphone 21 and outputs the sound signal to the control section 12. The endoscope apparatus 1 is capable of storing sound together with an endoscopic image and reproducing the sound.

(Action)

Next, display processing of a live image L, which is an endoscopic image, in the endoscope apparatus 1 of the first embodiment is explained.

Figure 2:
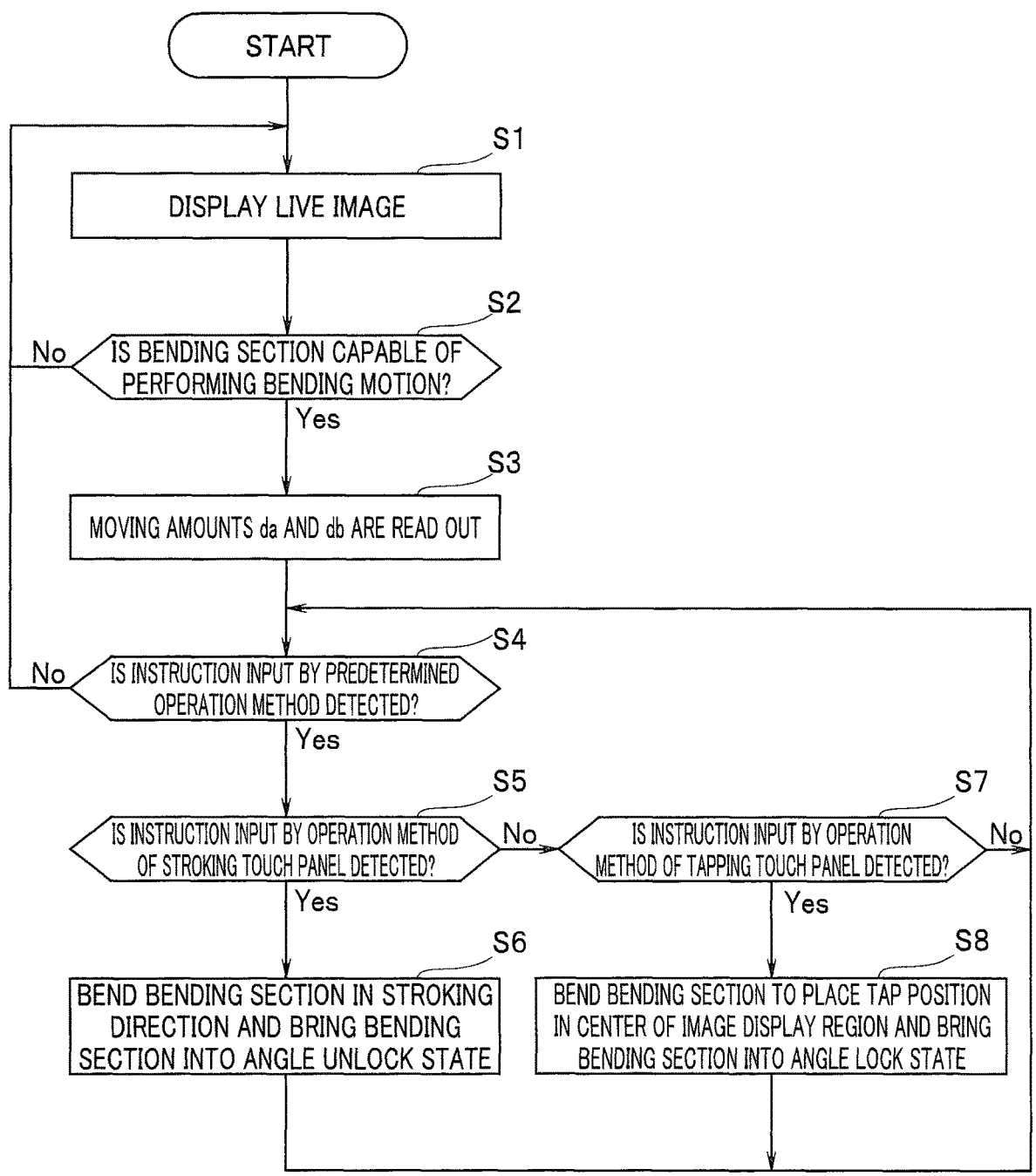
FIG. 2 is a flowchart showing an example of a flow of display processing of a live image of the endoscope apparatus according to the first embodiment of the present invention.

FIG. 2 is a flowchart showing an example of a flow of the display processing of the live image L of the endoscope apparatus 1 according to the first embodiment of the present invention. FIG. 3 is a diagram showing an example of the live image L displayed on the display section 14 of the endoscope apparatus 1 according to the first embodiment of the present invention. FIG. 4 is a diagram schematically showing an example of the bending motion of the bending section 2a1 of the endoscope apparatus 1 according to the first embodiment of the present invention. FIG. 5 is a diagram showing an example of the live image L displayed on the display section 14 of the endoscope apparatus 1 according to the first embodiment of the present invention.

The display processing of the live image L shown in FIG. 2 is performed by, when an instruction input for a processing start is performed through the touch panel 14b or the operation section 15, the CPU 12a of the control section 12 reading out and executing a display processing program stored in the memory 12b.

The control section 12 displays the live image L (S1). The control section 12 outputs a control signal to the video signal processing circuit 13. The video signal processing circuit 13 generates the live image L on the basis of an image pickup signal inputted from the CCU 11, outputs the live image L to the LCD 14a, and causes the live image L to be displayed in the image display region A of the LCD 14a. For example, in FIG. 3, an example of display of the live image L of the turbine blade TB including the chip D in the image display region A is indicated by a solid line.

The control section 12 determines whether the bending section 2a1 is capable of performing the bending motion (S2). The control section 12 determines possibility of the driving of the actuator 2b and possibility of the bending motion of the bending section 2a1 referring to the state information including the power supply ON state/OFF state that the actuator 2b has. When the control section 12 determines that the bending motion of the bending section 2a1 is possible (S2: YES), the processing proceeds to S3. When the control section 12 determines that the bending motion of the bending section 2a1 is impossible (S2: NO), the processing returns to S1. When the bending motion is impossible, for example, when preparation for the driving of the actuator 2b is uncompleted immediately after power-on, the processing returns to S1.

The movement amounts da and db are read out (S3). In S3, the movement amount da corresponding to the instruction input by the operation method of stroking the touch panel 14b and the movement amount db of the instruction input by the operation method of tapping the touch panel 14b stored in the memory 12b are read out.

The control section 12 determines whether an instruction input by a predetermined operation method is detected (S4). The predetermined operation method is either the operation method of stroking the touch panel 14b or the operation method of tapping the touch panel 14b. When the control section 12 determines in S4 that the instruction input by the predetermined operation method is detected (S4: YES), the processing proceeds to S5. On the other hand, when the control section 12 determines that the instruction input by the predetermined operation method is not detected (S4: NO), the processing returns to S1.

The control section 12 determines whether the instruction input by the operation method of stroking the touch panel 14b is detected (S5). When the control section 12 determines in S4 that the instruction input by the operation method of stroking the touch panel 14b is detected (S5: YES), the processing proceeds to S6. On the other hand, when the control section 12 determines in S4 that the instruction input by the operation method of stroking the touch panel 14b is not detected (S5: NO), the processing proceeds to S7.

The control section 12 bends the bending section 2a1 in a stroking direction and brings the bending section 2a1 into the angle unlock state (S6). In S6, the control section 12 causes the bending section 2a1 to perform the bending motion in the stroking direction such that the live image L moves from a contact end position toward a contact start position and brings the bending section 2a1 into the angle unlock state. After S6, the processing returns to S4.

For example, when the instruction input is performed by the operation method of stroking the touch panel 14b from a left portion to a right portion with a finger H (FIG. 3), the control section 12 transmits a control signal to the actuator 2b. The actuator 2b causes the bending section 2a1 to perform the bending motion to turn to the right (RR in FIG. 4). Consequently, the chip D of the turbine blade TB moves from a right portion (an alternate long and two short dashes line in FIG. 3) to a left portion (a solid line in FIG. 3) of the LCD 14a. For example, when a display image is rotated 180 degrees and displayed, the actuator 2b causes the bending section 2a1 to perform the bending motion to turn to the left.

In S7, the control section 12 determines whether the instruction input by the operation method of tapping the touch panel 14b is detected. When the control section 12 determines in S4 that the instruction input by the operation method of tapping the touch panel 14b is detected (S7: YES), the processing proceeds to S8. On the other hand, when the control section 12 determines in S4 that the instruction input by the operation method of tapping the touch panel 14b is not detected (S7: NO), the processing returns to S4.

The control section 12 causes the bending section 2a1 to perform the bending motion to place a tapped position in the center of the image display region A and brings the bending section 2a1 into the angle lock state (S8). In S8, the control section 12 causes the bending section 2a1 to perform the bending motion such that the live image L moves from the tapped position toward a center portion of the image display region A and brings the bending section 2a1 into the angle lock state. After S8, the processing returns to S4.

For example, when the chip D (an alternate long and two short dashes line in FIG. 5) of the turbine blade TB displayed in an upper left portion of the image display region A is tapped by the finger H as shown in FIG. 5, the control section 12 causes the bending section 2a1 to perform the bending motion to turn to the upper left. Consequently, the chip D of the turbine blade TB moves to the center portion of the image display region A (a solid line in FIG. 5).

The processing in S1 to S8 configures the display processing of the live image L according to the first embodiment.

That is, in an operation control method of the endoscope apparatus 1, when a first instruction input by a first operation method is performed on a first instruction input section, first operation control, which is control of operation based on the first instruction input, is performed. When a second instruction input by a second operation method is performed on a second instruction input section disposed in the display section 14 that displays an endoscopic image obtained by picking up an image of the object with the image pickup section 2, second operation control, which is control of operation based on the second instruction input, is performed.

According to the first embodiment, with the operation method of stroking the touch panel 14b and the operation method of tapping the touch panel 14b, it is possible to perform the instruction inputs corresponding to the respective operation methods and the operation control of the bending motion of the bending section 2a1 corresponding to the instruction inputs and move and display the live image L.

Second Embodiment

In the first embodiment, the live image L is displayed in the image display region A of the LCD 14a. However, a reproduced image, which is an endoscopic image, may be displayed.

In explanation of a second embodiment, the same components as the components in other embodiments are denoted by the same reference numerals and signs and explanation of the components is omitted.

The video signal processing circuit 13 is configured to be capable of outputting a generated endoscopic image to the control section 12 as well.

In the control section 12, an endoscopic image inputted from the video signal processing circuit 13 is stored in the memory 12b. The control section 12 is capable of causing, via the video signal processing circuit 13, the endoscopic image stored in the memory 12b to be displayed in the image display region A of the LCD 14a as a reproduced image. A reproduced image having a size larger than a display range to be displayed in the image display region A is stored in the memory 12b so as to be scrollable.

When an instruction input by the operation method of stroking the touch panel 14b is performed, the control section 12 performs, on the basis of the movement amount da, operation control of image processing for scrolling a display range of the object on the reproduced image from a contact end position toward a contact start position and according to a distance from the contact end position to the contact start position.

When an instruction input by the operation method of tapping the touch panel 14b is performed, the control section 12 performs, on the basis of the movement amount db, operation control of image processing for scrolling the display range of the object on the reproduced image from a tapped position toward the center portion of the image display region A of the LCD 14a and according to a contact time period of the touch panel 14b.

According to the second embodiment, with the operation method of stroking the touch panel 14b and the operation method of tapping the touch panel 14b, it is possible to perform the instruction inputs corresponding to the respective operation methods and the operation control of the image processing corresponding to the instruction inputs and move and display the reproduced image.

Third Embodiment

In the first embodiment and the second embodiment, one endoscopic image is displayed on the LCD 14a. However, a plurality of endoscopic images may be displayed on the LCD 14a.

In a third embodiment, the display section 14 includes an image display region A1 where a live image L1 is displayed and an image display region A2 where a reproduced image L2 is displayed. The live image L1 and the reproduced image L2 configure a comparison image.

Figure 6:
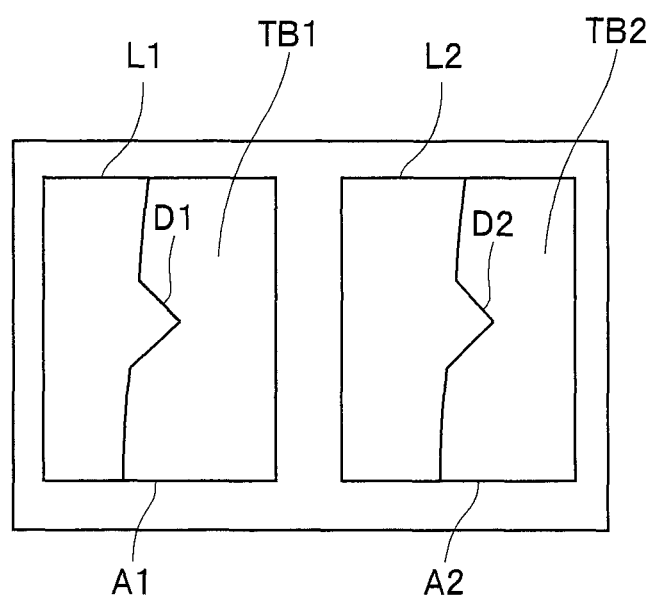
FIG. 6 is a diagram showing an example of a comparison image displayed on the display section of the endoscope apparatus according to a third embodiment of the present invention.

FIG. 6 is a diagram showing an example of a comparison image displayed on the display section 14 of the endoscope apparatus 1 according to the third embodiment of the present invention. In FIG. 6, the image display region A1 is disposed on a screen left side of the LCD 14a and the image display region A2 is disposed on a screen right side of the LCD 14a. As an example of the live image L1, a turbine blade TB1 including a chip D1 is displayed in the image display region A1. As an example of the reproduced image L2, a turbine blade TB2 including a chip D2 is displayed in the image display region A2. In the third embodiment, the same components as the components in the other embodiments are denoted by the same reference numerals and signs and explanation of the components is omitted.

When an instruction input by the operation method of stroking the touch panel 14b is performed in the image display region A1, the control section 12 moves an image pickup range of an object and brings the bending section 2a1 into the angle unlock state by causing the bending section 2a1 to perform bending motion in a stroking direction of the touch panel 14b.

When an instruction input by the operation method of tapping the touch panel 14b is performed in the image display region A1, the control section 12 moves the image pickup range of the object and brings the bending section 2a1 into the angle lock state by causing the bending section 2a1 to perform the bending motion such that the bending section 2a1 turns to a tapped position of the touch panel 14b.

When the instruction input by the operation method of stroking the touch panel 14b is performed in the image display region A2, the control section 12 scrolls the reproduced image L2 from a contact end position toward a contact start position and according to a distance from the contact end position to the contact start position. Note that, at this time, the control section 12 may perform control to scroll the reproduced image L2 in the same direction as the image display region A1 with the operation method of stroking the touch panel 14b. Consequently, it is possible to change a display range of the image display region A2 in the same sense as a sense of changing the display range of the image display region A1.

When the instruction input by the operation method of tapping the touch panel 14b is performed in the image display region A2, the control section 12 scrolls the reproduced image L2 from a tapped position toward a center portion of the image display region A2 and according to a contact time period of the touch panel 14b.

Consequently, the live image L1 and the reproduced image L2 are displayed on the LCD 14a. A surgeon can observe the live image L1 while comparing the live image L1 with the reproduced image L2.

According to the third embodiment, the live image L1 and the reproduced image L2 are displayed on the LCD 14a. With the operation method of stroking the touch panel 14b and the operation method of tapping the touch panel 14b, it is possible to perform, on each of the live image L1 and the reproduced image L2, the instruction inputs corresponding to the respective operation methods and the bending motions and the operation control of the image processing corresponding to the instruction inputs and move and display the live image L1 and the reproduced image L2.

Fourth Embodiment

In the third embodiment, the live image L1 and the reproduced image L2 are displayed on the LCD 14a. However, the live image L1 and a measurement image L3 may be displayed on the LCD 14a.

Figure 7:
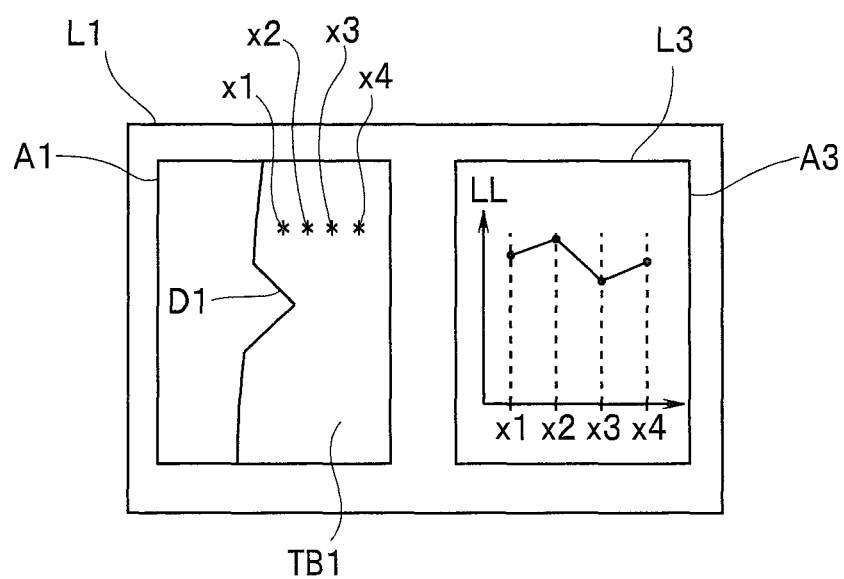
FIG. 7 is a diagram showing an example of a measurement image displayed on the display section of the endoscope apparatus according to a fourth embodiment of the present invention.

FIG. 7 is a diagram showing an example of the measurement image L3 displayed on the display section 14 of the endoscope apparatus 1 according to a fourth embodiment of the present invention. In explanation of the fourth embodiment, the same components as the components in the other embodiments are denoted by the same reference numerals and signs and explanation of the components is omitted.

In the fourth embodiment, the display section 14 includes the image display region A1 of the live image L1 and an image display region A3 of the measurement image L3. In FIG. 7, the image display region A1 where the live image L1 is displayed is disposed on the screen left side of the display section 14 and the image display region A3 where the measurement image L3 is displayed is disposed on the screen right side of the display section 14.

An optical adapter for stereoscopic measurement 4a is attached to the insertion section 2a (an alternate long and two short dashes line in FIG. 1). The optical adapter for stereoscopic measurement 4a includes not-shown two observation windows and gives two optical images of an object having a parallax each other to an image pickup surface of the image pickup device of the endoscope 2.

The video signal processing circuit 13 generates two endoscopic images having a parallax each other from an image pickup signal inputted via the CCU 11, outputs the endoscopic images to the control section 12, and causes the memory 12b to store the endoscopic images.

The control section 12 is capable of reading out the endoscopic images stored in the memory 12b, performing predetermined measurement concerning the object, and causing the display section 14 to display a measurement result.

More specifically, the control section 12 calculates, on the basis of the two endoscopic images having the parallax each other, interval lengths LL from a distal end of the insertion section 2a to predetermined characteristic points x1, x2, x3, and x4 fixedly disposed in the image display region A3 and outputs the interval lengths LL to the video signal processing circuit 13.

When the interval lengths LL to the predetermined characteristic points x1, x2, x3, and x4 are inputted from the control section 12, the video signal processing circuit 13 generates the measurement image L3 and causes the measurement image L3 to be displayed in the image display region A3. In FIG. 7, an example of the measurement image L3 is shown in which the interval lengths LL from the distal end of the insertion section 2a to the characteristic points X1, X2, X3, and X4 are shown.

In the image display region A1, when an instruction input by the operation method of stroking the touch panel 14b is performed, the control section 12 scrolls, on the basis of the movement amount da, the live image L1 from a contact end position toward a contact start position and according to a distance from the contact end position to the contact start position. On the other hand, when an instruction input by the operation method of tapping the touch panel 14b is performed, the control section 12 scrolls, on the basis of the movement amount db, the live image L1 from a tapped position toward a center portion of the image display region A1 and according to a contact time period of the touch panel 14b.

When the live image L1 is scrolled, the control section 12 calculates the interval lengths LL from the distal end of the insertion section 2a to the predetermined characteristic points x1, x2, x3, and x4 with respect to the live image L1 after the scrolling and outputs the interval lengths LL to the video signal processing circuit 13. Then, the video signal processing circuit 13 generates the measurement image L3 and causes the measurement image L3 to be displayed in the image display region A3.

According to the fourth embodiment, the live image L1 and the measurement image L3 are displayed on the LCD 14a. With the operation method of stroking the touch panel 14b and the operation method of tapping the touch panel 14b, it is possible to perform, on the live image L1, the instruction inputs corresponding to the respective operation methods and the bending motions and the operation control of the measurement processing corresponding to the instruction inputs and move and display the live image L1 and the measurement image L3.

Fifth Embodiment

In the first embodiment and the second embodiment, the operation control for moving the live image L or the reproduced image L2 is performed. However, operation control for moving an image for operation may be performed.

Figure 8:
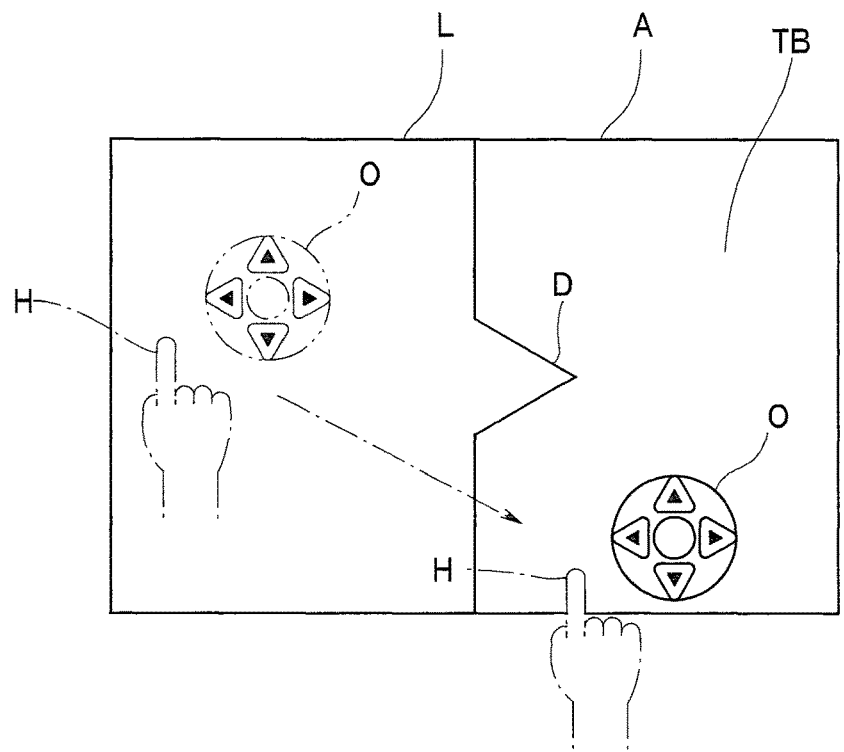
FIG. 8 is a diagram showing an example of an image for operation displayed on the display section of the endoscope apparatus according to a fifth embodiment of the present invention.
Figure 9:
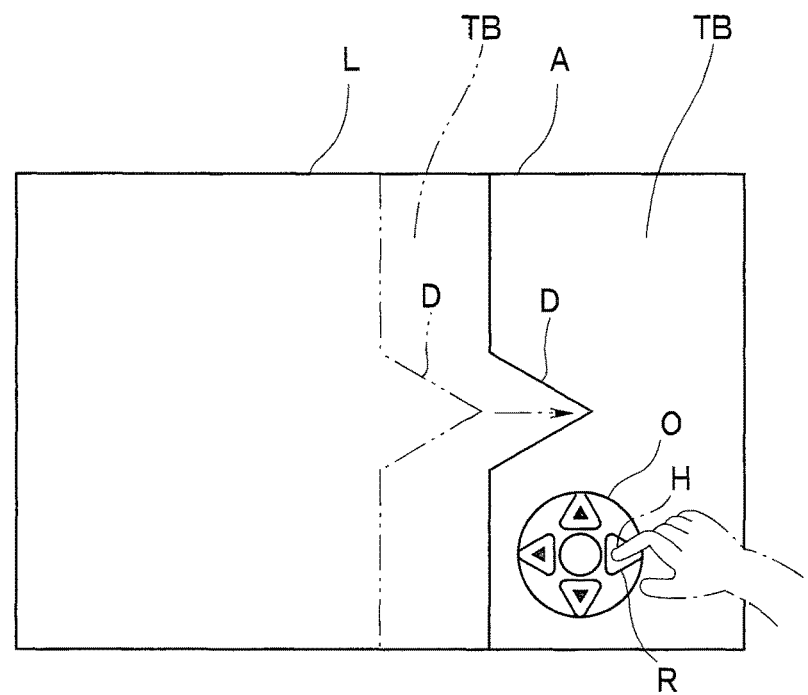
FIG. 9 is a diagram showing the example of the image for operation displayed on the display section of the endoscope apparatus according to the fifth embodiment of the present invention.

FIG. 8 and FIG. 9 are diagrams showing an example of an image for operation displayed on the display section 14 of the endoscope apparatus 1 according to a fifth embodiment of the present invention. In explanation of the fifth embodiment, the same components as the components in the other embodiments are denoted by the same reference numerals and signs and explanation of the components is omitted.

In the fifth embodiment, the video signal processing circuit 13 is configured to be capable of superimposing and disposing a movable image for operation on the live image L and causing the LCD 14a to display, in the image display region A of the LCD 14a, the live image L on which the image for operation is superimposed and disposed. In FIG. 8 and FIG. 9, a direction indication button O having a function of moving the live image L is shown as an example of the image for operation. Note that, in the fifth embodiment, an image displayed in the image display region A may be the reproduced image L2 rather than the live image L.

In the endoscope apparatus 1, an instruction input for moving the direction indication button O can be performed by the operation method of stroking the touch panel 14b.

In the endoscope apparatus 1, an instruction input for exhibiting a function corresponding to an operation of the direction indication button O can be performed by an operation method of tapping the direction indication button O of the touch panel 14b. More specifically, in the endoscope apparatus 1, an instruction input for moving the live image L can be performed by tapping a direction key of the direction indication button O displayed on the touch panel 14b.

When the instruction input by the operation method of stroking the touch panel 14b is performed by the finger H, the control section 12 moves, on the basis of the movement amount da, the direction indication button O from a contact start position toward a contact end position and according to a distance from the contact start position to the contact end position.

In FIG. 8, when the touch panel 14b is stroked from an upper left portion to a lower right portion by the finger H, the direction indication button O moves from the upper left portion (an alternate long and two short dashes line) to the lower right portion (a solid line).

Note that the instruction input by the operation method of stroking the touch panel 14b may be a drag operation of touching the direction indication button O with the finger H and sliding the finger H on the touch panel 14b or may be an operation of stroking a region other than the direction indication button O. In FIG. 8, an example of an operation of stroking a left downward direction of the direction indication button O, that is, a region other than the direction indication button O is shown.

When the instruction input by the operation method of tapping the direction key of the direction indication button O with the finger H is performed, the control section 12 moves, on the basis of the movement amount db, the live image L in directions corresponding to tapped respective direction keys and according to a contact time period of the touch panel 14b.

In FIG. 9, when a right direction key R of the direction indication button O is tapped by the finger H, the live image L moves from a center portion (an alternate long and two short dashes line) to a right portion (a solid line).

According to the fifth embodiment, the operation control for causing the bending section 2a1 to perform the bending motion is performed by the operation method of tapping the touch panel 14b and the operation control for the image processing for moving the direction indication button O is performed by the operation method of stroking the touch panel 14*b*. It is possible to move a display range of the live image L. It is possible to immediately move the direction indication button O to prevent a part desired to be observed of the live image L from being hidden by the direction indication button O.

Sixth Embodiment

In the first, second, third, fourth, and fifth embodiments, the operation control corresponding to the operation method of stroking the touch panel 14*b* and the operation control corresponding to the operation method of tapping the touch panel 14*b* are performed. However, operation control corresponding to an operation method of operating the operation section 15, which is a first instruction input section, and operation control corresponding to an operation method of operating the touch panel 14*b*, which is a second instruction input section, may be performed.

Figure 10:
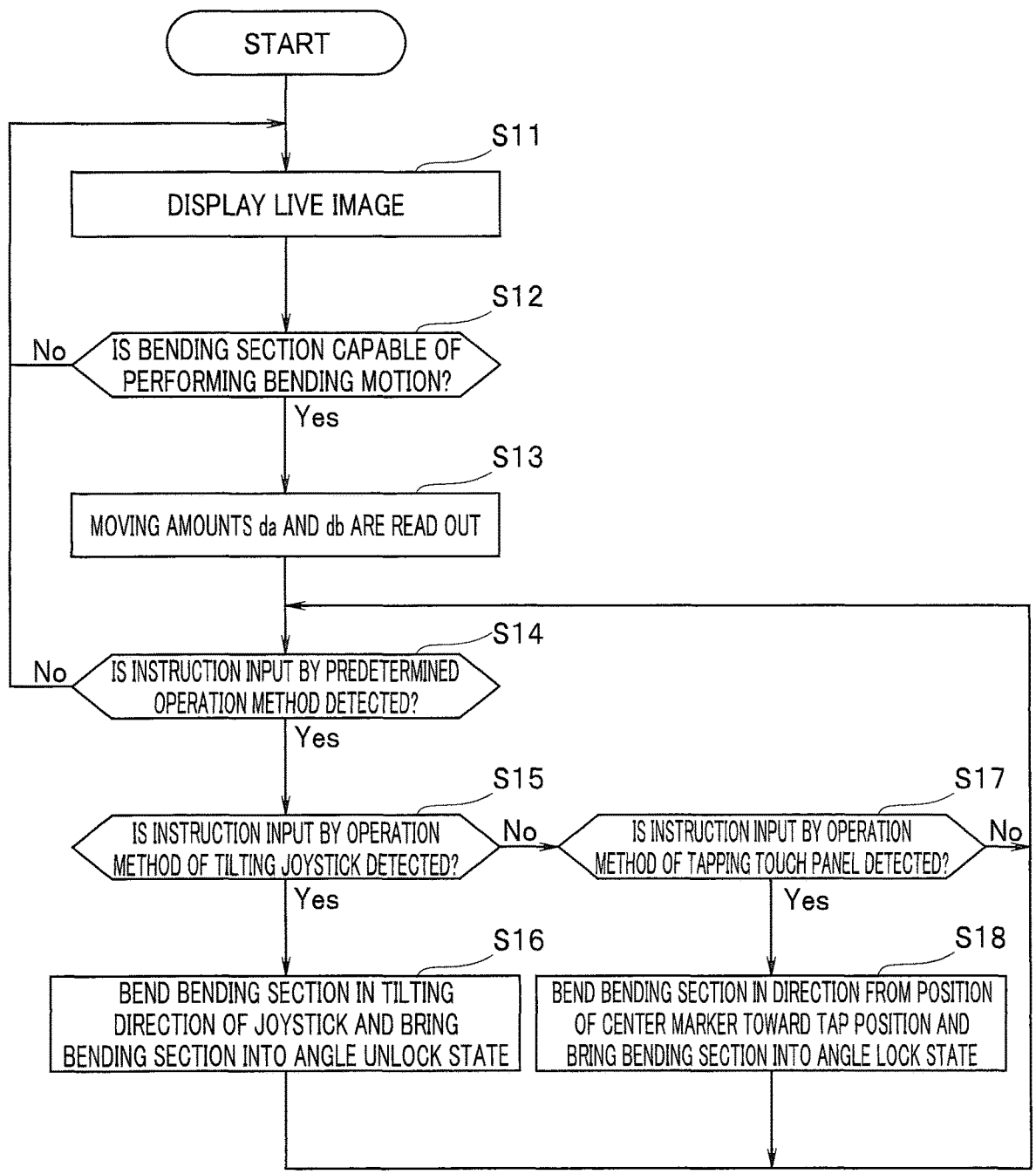
FIG. 10 is a flowchart showing an example of a flow of display processing of a live image of the endoscope apparatus according to a sixth embodiment of the present invention.
Figure 11:
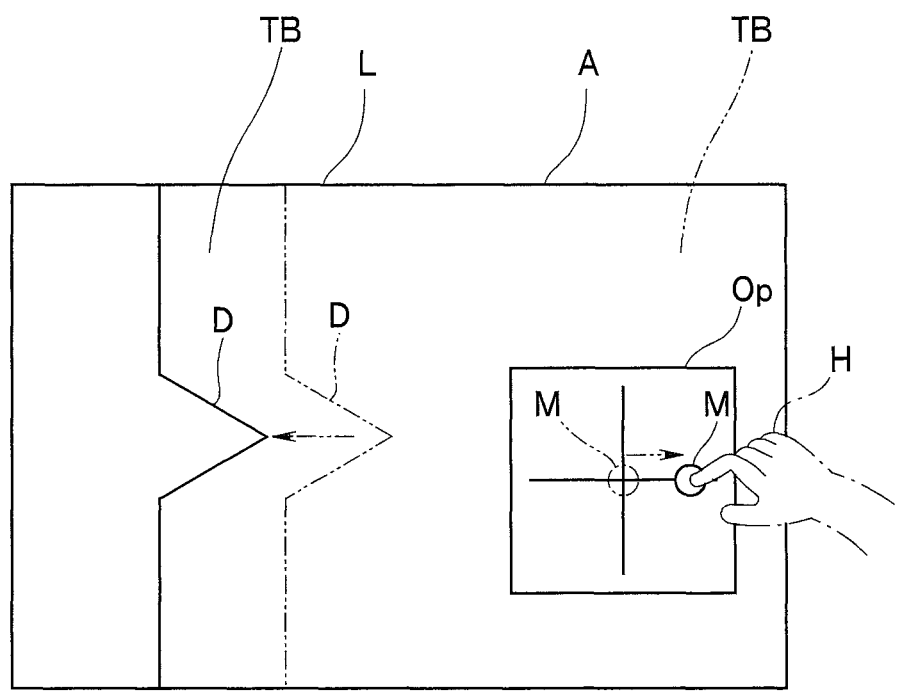
FIG. 11 is a diagram showing an example of an image for operation displayed on the display section of the endoscope apparatus according to the sixth embodiment of the present invention.

FIG. 10 is a flowchart showing an example of a flow of display processing of the live image L of the endoscope apparatus 1 according to a sixth embodiment of the present invention. FIG. 11 is a diagram showing an example of an image for operation displayed on the display section 14 of the endoscope apparatus 1 according to the sixth embodiment of the present invention. In explanation of the sixth embodiment, the same components as the components in the other embodiments are denoted by the same reference numerals and signs and explanation of the components is omitted.

In the sixth embodiment, rough movement for causing the bending section 2*a*1 to perform a large bending motion in a direction in which the joystick J is tilted is performed and fine movement for causing the bending section 2*a*1 to perform a small bending motion in a direction indicated by an operation panel Op, which is an image for operation, is performed.

With the joystick J, it is possible to perform, on the basis of the movement amount da, an instruction input for the bending motion of the bending section 2*a*1 such that a display range of an object on an endoscopic image moves. With the joystick J, it is also possible to perform an instruction input for angle unlock. For example, when the joystick J is tilted by the finger H, the bending motion of the bending section 2*a*1 is performed such that the display range moves by a distance corresponding to a tilting angle of the joystick J in a direction in which the joystick J is tilted. The bending section 2*a*1 is then brought into the angle unlock state.

The operation panel Op is displayed on the image display region A. The operation panel Op includes a marker M indicating a bending direction of the bending section 2*a*1. The marker M is disposed in a predetermined position indicating a center when the bending section 2*a*1 is in a neutral state in which the bending section 2*a*1 is not bent. When the bending section 2*a*1 is bent, the marker M moves by a distance of movement of a distal end position of the bending section 2*a*1 in a direction in which the distal end position of the bending section 2*a*1 moves. When the joystick J is tilted and the bending section 2*a*1 is bent, the marker M also moves according to a bending motion of the bending section 2*a*1.

With the operation panel Op, it is also possible to perform an instruction input for the bending motion of the bending section 2*a*1 such that the display range moves on the basis of the movement amount db. With the operation panel Op, it is also possible to perform an instruction input for angle lock. The movement amount db is set smaller than the movement amount da. For example, when a region in the operation panel Op is tapped by the finger H, the bending motion of the bending section 2*a*1 is performed such that the marker M moves toward a tapped position until the marker M moves to the same position as the tapped position or the finger H separates from the operation panel Op. The bending section 2*a*1 is then brought into the angle unlock state.

Note that the operation panel Op may be hidden only while the instruction input by the joystick J is performed to prevent an instruction input from being performed simultaneously with the instruction input by the joystick J. After the instruction input by the joystick J ends, the operation panel Op may be displayed again.

Note that, as explained in the fifth embodiment, the instruction input for moving the operation panel Op may be performed by the operation method of stroking the touch panel 14*b*.

Display processing of the live image L of the endoscope apparatus 1 according to the sixth embodiment is explained.

Processing in S11 to S12 is the same as S1 to S2. Therefore, explanation of the processing is omitted.

The movement amounts da and db are read out (S13).

The control section 12 determines whether an instruction input by a predetermined operation method is detected (S14). The predetermined operation method is either the operation method of tilting the joystick J or the operation method of tapping the touch panel 14*b*. When the control section 12 determines that the instruction input by the predetermined operation method is detected (S14: YES), the processing proceeds to S15. On the other hand, when the control section 12 determines that the instruction input by the predetermined operation method is not detected (S14: NO), the processing returns to S11.

The control section 12 determines whether an instruction input by the operation method of tilting the joystick J is detected (S15). When the control section 12 determines that the instruction input by the operation method of tilting the joystick J is detected (S15: YES), the processing proceeds to S16. On the other hand, when the control section 12 determines that the instruction input by the operation method of tilting the joystick J is not detected (S15: NO), the processing proceeds to S17.

The control section 12 bends the bending section 2*a*1 in a direction in which the joystick J is tilted and brings the bending section 2*a*1 into the angle unlock state (S16). The control section 12 bends the bending section 2*a*1 by a distance corresponding to a tilting amount of the joystick J in the direction in which the joystick J is tilted and moves a display range of an object on an endoscopic image. The control section 12 brings the bending section 2*a*1 into the angle unlock state. After S16, the processing returns to S14.

In S17, the control section 12 determines whether an instruction input by the operation method of tapping the touch panel 14*b* is detected. When the control section 12 determines that the instruction input by the operation method of tapping the touch panel 14*b* is detected (S17: YES), the processing proceeds to S18. On the other hand, when the control section 12 determines that the instruction input by the operation method of tapping the touch panel 14*b* is not detected (S17: NO), the processing returns to S14.

The control section 12 bends the bending section 2*a*1 in a direction from a position of the marker M toward a tapped position and brings the bending section 2*a*1 into the angle lock state (S18). The control section 12 bends the bending section 2*a*1 by a distance corresponding to a contact time period of the touch panel 14*b* in a direction from a position of a center marker M toward the tapped position and moves the display range of the object on the endoscopic image. The control section 12 brings the bending section 2a1 into the angle lock state. After S18, the processing returns to S14.

For example, when a right portion of the operation panel Op is tapped by the finger H as shown in FIG. 11, the control section 12 causes the bending section 2a1 to perform the bending motion to the right. The chip D of the turbine blade TB moves to the left on the image display region A (a solid line in FIG. 11). The marker M moves to the right on the operation panel Op.

The processing in S11 to S18 explained above configures the display processing of the live image L according to the sixth embodiment.

That is, in the sixth embodiment, a first operation method is an operation method of operating the joystick J and a second operation method is an operation method of operating the touch panel 14b. More specifically, the second operation method is an operation method of operating the touch panel 14b with an image for operation.

First operation control includes operation control for moving the display range of the object on the endoscopic image by a distance corresponding to a tilting amount of the joystick J in a direction in which the joystick J is tilted. Second operation control includes operation control for moving the display range by a distance corresponding to a contact time period of the touch panel 14b in a direction from a position of the marker M to a contact position of the finger H on the touch panel 14b.

According to the sixth embodiment, with the operation method of tilting the joystick J and the operation method of tapping the touch panel 14b, it is possible to perform the instruction inputs corresponding to the respective operation methods and the operation control of the bending motion of the bending section 2a1 corresponding to the instruction inputs and move and display the live image L.

Note that, in the first to fifth embodiments, the first operation method is the operation method of stroking the touch panel 14b and the second operation method is the operation method of tapping the touch panel 14b. However, the first operation method may be the operation method of tapping the touch panel 14b and the second operation method may be the operation method of stroking the touch panel 14b.

Note that, in the embodiments, the image display region A1 is disposed on the screen left side of the LCD 14a and the image display region A2 is disposed on the screen right side of the LCD 14a. However, the image display region A1 and the image display region A2 may be reversely disposed on the left and right each other, may be disposed vertically, or may be disposed to overlap each other.

Note that, in the first embodiment, the second embodiment, the third embodiment, and the fourth embodiment, when the instruction input by the operation method of stroking the touch panel 14b is performed, the operation control is performed such that the live images L and L1, the reproduced image L2, and the measurement image L3 are moved from the contact end position toward the contact start position. However, the operation control may be performed such that the live images L and L1, the reproduced image L2, and the measurement image L3 are moved from the contact start position toward the contact end position. That is, a direction of the instruction input by the operation method of stroking the touch panel 14b may be adjusted to a bending direction of the bending section 2a1 or may be adjusted to a scroll direction of an endoscopic image displayed on the LCD 14a.

Note that, in the first embodiment, the third embodiment, and the fourth embodiment, when the instruction input by the operation method of stroking the touch panel 14b is performed, the bending section 2a1 is caused to perform the bending motion and is brought into the angle unlock state. However, the bending section 2a1 may be brought into the angle unlock state without being caused to perform the bending motion. Consequently, a surgeon is capable of performing an instruction input for only bringing the bending section 2a1 into the angle unlock state.

Note that, in the sixth embodiment, the second operation control is operation control for moving the display range by a distance corresponding to a contact time period of the touch panel 14b in a direction from a current bending direction toward a contact position of the finger H on the touch panel 14b. However, the second operation control may be operation control for moving the display range from a contact end position toward a contact start position of the finger H or from the contact start position toward the contact end position on the touch panel 14b.

The present invention is not limited to the embodiments explained above. Various changes, alterations, and the like are possible in a range in which the gist of the present invention is not changed.

According to the present invention, it is possible to provide the endoscope apparatus 1 capable of performing, according to a predetermined operation method for the instruction input section, an instruction input corresponding to the operation method and operation control corresponding to the instruction input, an operation control method for the endoscope apparatus 1, and a storage medium having an operation control program for the endoscope apparatus 1 stored therein.

What is claimed is:
1. An endoscope apparatus comprising:
a display configured to display an endoscopic image obtained by picking up an image of an object with an image pickup sensor;
a touch panel provided in the display;
an insertion section including a bendable bending section;
an operation section including at least one operation device; and
a processor, wherein the processor is configured to:
determine whether a first instruction input by the operation section is detected,
perform first operation control on the bending section when determining that the first instruction input is detected,
determine whether a second instruction input by the touch panel is detected,
perform second operation control different from the first operation control on the bending section when determining that the second instruction input is detected;
perform bending control of the bending section based on a first movement amount, in the first operation control; and
perform bending control of the bending section based on a second movement amount, in the second operation control, the second movement amount being smaller than the first movement amount.
2. The endoscope apparatus according to claim 1, wherein the at least one operation device is a joystick, and
the first instruction input is an instruction input by an operation method of operating the joystick.

3. The endoscope apparatus according to claim 2, wherein
the first operation control includes operation control for causing the bending section to perform a bending motion by a distance corresponding to a tilting amount of the joystick in a direction in which the joystick is tilted, and
the second operation control includes operation control for causing the bending section to perform the bending motion by a distance corresponding to a contact time period of the touch panel in a direction toward a contact position of a finger.

4. The endoscope apparatus according to claim 2, wherein
the first operation control includes operation control for causing the bending section to perform a bending motion in a direction in which the joystick is tilted, and
the second operation control includes operation control for causing the bending section to perform the bending motion to move from a contact end position toward a contact start position of a finger on the touch panel or move from the contact start position toward the contact end position.

5. The endoscope apparatus according to claim 2, wherein
the display is configured for displaying an image for operation, and
the second instruction input is an instruction input by an operation method of operating the touch panel with the image for operation.

6. The endoscope apparatus according to claim 5, wherein the operation panel is hidden while the instruction input by the joystick is performed.

7. The endoscope apparatus according to claim 1, wherein the second instruction input is an instruction input by an operation method of stroking the touch panel.

8. The endoscope apparatus according to claim 1, wherein the second instruction input is an instruction input by an operation method of tapping the touch panel.

9. An operation control method for an endoscope apparatus comprising:
determining whether a first instruction input by an operation section including at least one operation device is detected;
performing first operation control on a bendable bending section provided in an insertion section when determining that the first instruction input is detected;
determining whether a second instruction input by a touch panel provided in a display configured to display an endoscopic image obtained by picking up an image of an object with an image pickup sensor is detected;
performing second operation control different from the first operation control on the bending section when determining that the second instruction input is detected;
performing bending control of the bending section based on a first movement amount, in the first operation control; and
performing bending control of the bending section based on a second movement amount, in the second operation control, the second movement amount being smaller than the first movement amount.

10. A non-transitory storage medium having an operation control program for an endoscope apparatus stored therein, the operation control program causing a computer to execute:
a code for determining whether a first instruction input by an operation section is detected;
a code for performing first operation control on a bending section when determining that the first instruction input is detected;
a code for determining whether a second instruction input by a touch panel is detected;
a code for performing second operation control different from the first operation control on the bending section when determining that the second instruction input is detected;
a code for performing bending control of the bending section based on a first movement amount, in the first operation control; and
a code for performing bending control of the bending section based on a second movement amount, in the second operation control, the second movement amount being smaller than the first movement amount.

* * * * *